United States Patent [19]

O'Lenick

[11] Patent Number: 4,476,045

[45] Date of Patent: Oct. 9, 1984

[54] SURFACTANT

[75] Inventor: Anthony J. O'Lenick, Fairlawn, N.J.

[73] Assignee: Henkel Corporation, Minneapolis, Minn.

[21] Appl. No.: 377,646

[22] Filed: May 13, 1982

[51] Int. Cl.$^3$ .............................................. C11D 1/18
[52] U.S. Cl. .................................. 252/545; 252/526; 252/550; 252/554; 252/558; 252/DIG. 4; 252/DIG. 14; 260/501.19; 260/458 R; 8/142
[58] Field of Search .............. 252/526, 545, 550, 554, 252/544, 555, 558, 551, DIG. 14, 548, 559; 260/501.19, 458 R; 8/142

[56] References Cited

U.S. PATENT DOCUMENTS

| | | | |
|---|---|---|---|
| 2,673,215 | 3/1954 | Keenan et al. | 252/548 |
| 2,758,093 | 8/1956 | Ernst et al. | 252/118 |
| 2,970,158 | 1/1961 | Levis | 252/548 |
| 3,549,544 | 12/1970 | Johnson | 252/545 |
| 3,594,323 | 7/1971 | Taylor et al. | 252/545 |
| 3,709,838 | 1/1973 | Mausner | 252/559 |
| 4,124,517 | 11/1978 | Hisamoto et al. | 252/153 |
| 4,263,179 | 4/1981 | Schmolka | 252/548 |

FOREIGN PATENT DOCUMENTS

| | | |
|---|---|---|
| 2512616 | 9/1975 | Fed. Rep. of Germany . |
| 2644289 | 4/1978 | Fed. Rep. of Germany . |
| 1047771 | 11/1966 | United Kingdom . |
| 1084061 | 9/1967 | United Kingdom . |

*Primary Examiner*—Paul Lieberman
*Assistant Examiner*—Hoa Van Le
*Attorney, Agent, or Firm*—J. Daniel Wood; Ernest G. Szoke

[57] ABSTRACT

This invention describes high active content surfactant products which are neutralized with an amine which is a secondary or tertiary amine containing at least one group of three carbon atoms attached to the nitrogen atom; and which further contain at least one alcoholic hydroxy group; and which is alpha or beta substituted with respect to the nitrogen atom.

20 Claims, No Drawings

SURFACTANT

BACKGROUND OF THE INVENTION

1. Field of the Invention

This invention relates to the detergent industry.

2. Description of the Art Practices

Sulfated organic surfactants have been known for many years, the first having been prepared by Dumas in 1836. When organic sulfate surfactants are manufactured a difficulty exists in obtaining a high active content product. In some applications this is unimportant as the inactive portion of the composition will either be water and/or inorganic salts. The water is present as a product from the neutralization reaction and from use as a solvent, i.e. aqueous caustic. If one is directly manufacturing a detergent product for use as a household dishwashing composition then the amount of water in the formulation is somewhat immaterial as these products contain a high portion of water. Similarly the presence of inorganic salts are of no great consequence when the end product is a solid as the inorganic sulfate salt aids in forming crisp granules.

It is however highly desirable to obtain high active content organic sulfate products when the surfactants are manufactured for sale to customers who desire to have an anhydrous product to lower shipping costs or to those who wish to obtain a high active formulation. Similarly oil field applications of such materials where foaming is desired only at the well site and not prior to placing the surfactant in the well require specialized products with which the present invention is concerned.

There have been attempts in the art to manufacture what are essentially anhydrous surfactant products. For instance it is possible to obtain alkyl sulfates or alkyl ether sulfates at up to 30 percent solids in water without encountering any great difficulty. In current practice an alcohol or alcohol ethoxylate are reacted with a sulfating agent to form a sauer ester and thereafter the sauer ester is neutralized with aqueous caustic to give the sodium salt. By sauer ester it is meant that the alcohol, ethoxylated alcohol, olefin, or alkylbenzene which can be converted to a sulfate (sulfonate) salt is first reacted with a sulfating agent to give the sauer ester which is in fact an acid ester.

This technology allows the alkyl ether sulfate or alkyl sulfate to be obtained in concentrations of 20 to 40 percent by weight in water. A particular difficulty with this technology is however that the sauer ester must be mixed extremely thoroughly and rapidly with the caustic to avoid hydrolysis of the sauer ester back to the starting unsulfated material. Where this hydrolysis occurs the product will contain for example the starting alcohol, and as the hydrolysis also generates sulfuric acid, sodium sulfate will also be formed. As this reaction invariably takes place to some extent the active content is lost and a fatty alcohol is generated in the product which is of little use, if not a detriment to the product. Moreover the sodium sulfate formed in the reaction mixture complicates further processing and adds nothing to the product when a high active concentration is desired.

In order to alleviate the problems described above it has been suggested that products with a 60 percent active concentration of an alkyl sulfate or alkyl ether sulfate may be formulated.

However to allow processing of such products it has been found necessary to utilize substantial amounts of solubilizing agents such as glycols or lower monohydric alcohols. This is despite the fact that the product is already dissolved in 40% water. These hydrotropes aid in maintaining the product in a semi-fluid state but also have an effect on the ability of the product to remain clear when in a liquid state.

As previously noted the caustic neutralization step will result in a small amount of the starting alcohol and sodium sulfate in the product. Moreover, the processing also inherently leaves substantial amounts of water which again are not desired in some applications.

Even with this aforedescribed technology the high active content is particularly subject to the hydrolysis previously discussed, and it is necessary to vigorously mix the product. It is further known that it is possible to obtain alkyl sulfates and alkyl ether sulfates with concentrations as high as 70 percent by weight solids with the remainder being substantially aqueous if proper mixing techniques are used in the neutralization step.

Unfortunately the mixing system for such a product still allows some hydrolysis to occur thereby generating the starting alcohol and the inorganic sulfate salt. Moreover, when a 70 percent active concentration is obtained the product has the consistency of vaseline and during the processing the viscosity may reach 2 million cps. It has also been noted that when such products are sold that the end user of the formulation when diluting out the vaseline type product with water will again encounter the 2 million cps viscosity thus limiting the use of such products to a low feed rate into a reaction or alternatively presents the need for substantial investment in mixing equipment.

It has been suggested in U.S. Pat. No. 3,728,265 issued Apr. 17, 1973 to Chella et al, that high foaming liquid detergent compositions may be formulated for use in non-pressurized containers wherein the product contains a compressible water-insoluble gas, an organic solvent such as propylene glycol, a water-soluble anionic detergent, and an alkanolamide. U.S. Pat. No. 3,850,831 to Hellsten et al describes liquid detergent compositions containing a surfactant, a peroxide bleaching agent and a polyhydric alcohol in a substantially anhydrous formulation.

It is described in Canadian Pat. No. 1,028,957 to Mackles to form a detergent product which is a combination of a propellant, and a material which is a coconut oil diethanolamide neutralized with lauryl ether sulfate and further containing isostearic acid diethanolamide.

Therefore there remains, and the present invention deals with the obtaining of high active content formulations of an alkyl ether sulfate, alkyl benzene sulfonate, olefin sulfonate or alkyl sulfate containing only minimal amounts of inorganic salts and minimal amounts of the starting alcohol. Such products are also desirably to be liquids of low viscosity and high clarity with limited water content. Products of the present invention are useful for any of the purposes that such surfactants are used including personal care products, household, institutional and industrial detergents; including such uses as shampoos, bubble baths, hand soaps, emulsions, emulsion polymerization, oil field chemicals, hard surface cleaners, laundry and dishwashing detergents, paper processing, gypsum board formers and other uses.

Throughout the specification and claims percentages and ratios are by weight, pressures are gauge and temperatures are Celsius unless otherwise indicated. The terms alkyl ether sulfate, alkyl alkoxy sulfate, alcohol ether sulfate and the like are used interchangably. The term organic anionic sulfate embraces the former materials as well as alkyl sulfate. For practical purposes the term sulfating agent also is used when referring to a sulfonating agent. Olefin sulfonate is used herein, however, it is recognized that the unsaturation is lost in the sulfation reaction giving an alpha-substituted sulfonate.

SUMMARY OF THE INVENTION

A surfactant comprising:

(a) an organic sulfate or sulfonate amine salt containing from about 8 to 22 carbon atoms in the anionic portion of the molecule; and, (b) a sufficient amount of an amine to neutralize the sulfate or sulfonate portion of component (a) wherein the amine is selected from the group consisting of secondary and tertiary amines, said amine containing at least one group of 3 carbon atoms attached to the nitrogen atom; at least one alcoholic hydroxy group; and being alpha or beta branched with respect to the nitrogen atom.

DETAILED DESCRIPTION OF THE INVENTION

In the detergent art it is well known to manufacture a sauer ester from a fatty alcohol or a fatty alcohol alkoxylate. The reader is referred to U.S. Pat. No. 3,971,815 issued July 27, 1976 to Sagel et al for a description of various methods of preparing the sauer ester of a alkoxylated alcohol or an alcohol sulfate. A sauer ester is defined as the acid product of the sulfation reaction prior to neutralization. The amount of amine (cationic) component (b) discussed later is included in the amount of the organic anionic sulfate or sulfonate recited above to stoicheometrically balance the compound. In the present invention the processing of the alcohol sulfate or alcohol alkoxylate sulfate is substantially similar to that used in the art and accordingly such may be practiced in the present invention.

Whereas in the prior art caustic in an aqueous solution is used to neutralize the sauer ester, the present invention employs an amine which is substituted in the alpha or beta position to the nitrogen with carbon atoms. The amine moeity is highly branched near the nitrogen atom. While such products result in a neutralized product no water is generated and no water is needed as a carrier. If one used a concentrated caustic solution, the neutralized product would not be of sufficiently high active content as is desired in the present invention.

More particularly, the amine must contain at least one group of three carbon atoms attached to the amine nitrogen. The amine must further contain at least one alcoholic hydroxyl groups, i.e. a hydroxyl attached to a carbon atom. The amine is further defined as having alpha or beta branching with respect to the amine nitrogen, and the amine must be a secondary or tertiary amine.

While each of the above requirements must be met, it is possible to do so by varying the substituents. For instance diethanolamine is not suitable for the invention and does not fall within the definition given for the amine. However, if the remaining amine hydrogen is substituted for with a 2-methyl propyl group the amine is then functional. Similarly, if diethanolamine is substituted for by replacing one of the hydroxyethyl groups with a 2-hydroxypropyl group the definition is met and the compound is functional. It is noted that the alpha (beta) branching rule may be satisfied by using the alcoholic hydroxyl group to provide the branching. There is also no limit on the number of hydroxyl groups as long as there is one which is alcoholic. The carbon atom limitation of at least 3 carbon atoms in one group attached to the amine nitrogen may be satisfied by a simple alkyl group and there may be as few as 4 carbon atoms total in the amine, i. e. N-(2-hydroxypropyl)-N-(methyl)amine or N-(1-methylethyl)-N-(hydroxymethyl)amine. A preferred total carbon number for the amine is from 5 to 22, more preferably 6 to 20 carbon atoms. It is also desired that the amine contain a single nitrogen atom although some polynitrogen containing compounds may be used. It is also preferred that the amine component is a polyhydroxyl amine.

Preferred amines for use as the neutralizing agent include:

N,N-bis-(2-hydroxypropyl)amine;
N,N,N-tris-(2-hydroxypropyl)amine;
N-(2-hydroxyethyl)-N-(2-hydroxypropyl)amine;
N-(2-hydroxyethyl)-N-(2-hydroxybutyl)amine;
N-(2-hydroxybutyl)-N-(3-hydroxy-2-methylpropyl)amine;
N-(2-hydroxypropyl)-N-(butyl)amine;
N-(2-hydroxypropyl)-N-(2-hydroxybutyl)amine;
N,N,N',N'-tetrakis-(2-hydroxypropyl)ethylenediamine;
N,N-bis-(1-hydroxypropyl)amine; and
2,2-bis(hydroxymethyl)-2,2',2"-nitrilotriethanol.

An especially preferred mixture is that obtained by the reaction of propylene oxide and ammonia which gives a mono, di, and trisubstituted amine mixture. While the mono-substituted product is not useful per se it performs quite well in the mixture. Therefore N,N-bis-(2-hydroxypropyl)amine or N,N,N-tris-(2-hydroxypropyl)amine may be used alone, or together, and with N-(2-hydroxypropyl)amine.

The amount of the amine employed in the present invention is simply that necessary to convert the sulfate or sulfonate of the acid form to the salt of the amine. While lesser amounts might be employed, any remaining acid form left in the product would be able to hydrolize upon contact with water thereby resulting in a loss of active. The amine component forms the salt of the sulfate or sulfonate on an equivalent basis, i.e. one cationic nitrogen per sulfate or sulfonate group present.

Therefore the neutralization by the amine should be substantially complete. In fact it is desirable to use up to 10 percent, preferably up to 5 percent of the amine on a equivalent basis over that which is required to neutralize the sauer ester thereby assuring that the pH remains sufficiently high to prevent the degradation. It is noted, however, that the product is capable of functioning at pH's between 5 and 10, but that a neutral or slightly alkaline pH is preferred. The pH may be maintained by the amine of component (b) or another amine such as ethanolamine. The products obtained have high active content, are clear when mixed with water, and are obtained if desired as an essentially anhydrous product of low viscosity. Further, coventional hydrotropes are not required to obtain the above properties.

It has been found possible however when using the alpha or beta substituted amine to greatly increase the active content of the product by including an alkanolamide as described in the Summary of the Invention. The alkanolamide has been found to retard whatever degradation that the product would undergo during neutralization. It is therefore now possible to obtain high active contents where the product essentially contains only the neutralized sulfate (sulfonate) and a dialkanolamide. There may be small amounts of free amine, unreacted alcohol and a minor proportion, if any, of water and inorganic salt.

It is noted at this point that not only does sodium hydroxide not work as the neutralizing agent because of the hydrolysis which occurs (generating an inorganic salt and the starting material) but that several amines are also unsatisfactory in the present invention. For instance monoethanolamine, diethanolamine, triethanolamine, and diglycolamine are unsatisfactory in the present invention. These latter amines do not result in obtaining a liquid product of essentially 100 percent active ingredients but rather a low active content, solid product is obtained. Accordingly heat would have to be applied in order to allow the product to be processed thereby making a shipment in a tank wagon impractical if not impossible.

Thus by following the teachings of the present invention a product may be obtained which is a clear liquid having an active content nearing 100 percent. The solubility of the product when diluted out with water as would be done by a formulator is quite rapid requiring very little mixing to obtain a solution of the product. The product as obtained in the present invention has a high active content, is clear and homogeneous at ambient temperature. This product when diluted out is clear at all concentrations.

The starting alcohol is conveniently a linear material containing from 8 to 22 carbon atoms, preferably 12 to 18 carbon atoms. This material as previously noted is sulfated by conventional technology or is alkoxylated and thereafter sulfated. In most cases the alkoxylate is the ethoxylate and the average degree of ethoxylation is normally from 1 to 12 preferably 1 to 5 moles of the alkoxylate per mole of starting alcohol. It is also advantageous to prepare a mixture of alcohol and alcohol alkoxylate of from 30:1 to 1:30, preferably 10:1 to 1:10 by weight. In any case the alcohol or the alcohol alkoxylate is then sulfated by any number of convenient means including those described in U.S. Pat. No. 3,971,185 herein incorporated by reference. Without limiting the present invention the methods of sulfation include oleum (fuming sulfuric acid), chlorosulfonic acid, or film sulfation using $SO_3$. As noted previously up to this point obtaining the sauer ester in the manner indicated is conventional technology. Similarly the alkyl benzene or olefin is sulfonated to the acid.

The sauer ester is then combined with the amine and the alkanolamide by any simple mixing process. Conveniently the sauer ester is added to a mixture of the amine and the alkanolamide. As the invention gives a low viscosity product a substantial savings in mixing energy is observed.

The product may be further improved by including an alkanolamide. When employed, an alkanolamide of the formula $RC(O)N(CH_2CH_2OH)_2$ is used wherein R is an alkyl group having from 8-22 carbon atoms, preferably 10 to 20 carbon atoms. It is also noted that values of R corresponding to 12, 14, 16, or 18 carbon atoms are also highly desirable. It is noted, however, without any particular advantage in the present invention that the R values may be mixed. R is conveniently a saturated or unsaturated linear moeity.

The alkanolamide is conveniently utilized at levels of from about 10 to about 35 percent by weight, preferably from about 12 to 30%, most preferably 15% to 25% by weight based on the weight of amine salt (a) and the alkanolamide (c). It is noted at this point that the alkanolamide must be a dialkanolamide as the monoalkanolamides have been found not to be useful in the present invention. The use of the alkanolamide raises the viscosity slightly when the product is diluted. Raised viscosity is desired to avoid a runny product.

Where the alkanolamide is employed the organic sulfate or sulfonate salt is used as follows: The anionic sulfate or sulfonate is utilized in the present invention at from about 40% to about 90%, preferably from about 70% to about 88% most preferably 75% to 85% by weight.

A useful source of the dialkanolamide is a Kritchevsky product which is the precursor amide dissolved in an unreacted fatty acid alkanolamine soap. The fatty acid portion of the soap having the same definition as previously given for R. The presence of the soap in the Kritchevsky product helps foaming but the viscosity is lower when the product is diluted out with water.

For example a dishwashing product prepared according to this invention may be diluted out with water to give about 4-27% of component (a), 1-18% component (c) and 70% to 90% by weight water based on the weight of component (a), component (c) and the water. Preferably the foregoing materials are employed at 5-25%, 1-16%, and 73% to 88% by weight respectively.

The surfactant of the present invention may be used with all manner of other anionic, cationic, amphoeteric, and zuritherionic detergents.

The following are suggested embodiments of the present invention.

EXAMPLE I

Products of the present invention are prepared by obtaining the sauer ester of the sulfate (sulfonate) and the neutralization is conducted by mixing the various ingredients together. Formulations are shown below.

|  | A | B | C | D |
|---|---|---|---|---|
| Sauer Ester* | 53.2 | 59.1 | 51.59 | 51.71 |
| N—bis-(2-hydroxypropyl)amine | 26.8 | 30.9 | | |
| N—tris-(2-hydroxypropyl)amine | | | 28.41 | |
| N(2-hydroxyethyl)-N—(2-hydroxypropyl)amine | | | | 33.29 |

*lauryl sulfate

This example may be modified by using as the sauer ester an alkyl ether sulfate, an olefin sulfonate and or an alkyl benzene sulfonate.

The sauer ester is conveniently added to a preformed mixture of the amine and the alkanolamide. This facilitates mixing in that the viscosity of the resultant product is low.

The product may be further improved by including the aforementioned alkanolamides in the following suggested amounts in the formulation given above:

| A | B | C | D |
|---|---|---|---|
| 20 | 10 | 20 | 15 |

After the neutralization of the sauer ester, the product may be diluted to any concentration as hydrolysis is not possible in the neutralized system. The products have the advantages previously described.

What is claimed is:

1. A surfactant consisting essentially of the salt of
   (a) an acid selected from the group consisting of an organic sulfate or sulfonate in the acid form containing from about 8 to about 22 carbon atoms in the anionic portion of the molecule; and
   (b) a sufficient amount to substantially neutralize component (a) of an amine selected from the group consisting of N,N,N,-tris-(2-hydroxypropyl)amine; N-(2-hydroxyethyl)-N-(2-hydroxybutyl)amine; N-(2-hydroxybutyl)-N-(3-hydroxy-2-methylpropyl) amine; N-(2-hydroxypropyl)-N-(butyl)amine; N-(2-hydroxypropyl)-N-(2-hydroxybutyl amine; and 2,2-bis(hydroxymethyl)-2,2',2"-nitrilotriethanol and mixtures thereof.

2. The composition of claim 1 wherein component (a) is present at from 70 to 88 percent by weight of the composition.

3. The composition of claim 1 which is substantially non-aqueous.

4. The composition of claim 1 wherein component (b) is N,N,N-tris-(2-hydroxypropyl)amine.

5. The composition of claim 1 wherein component (b) is N-(2-hydroxyethyl)-N-(2-hydroxybutyl)amine.

6. The composition of claim 1 wherein component (b) is N-(2-hydroxybutyl)-N-(3-hydroxy-2-methylpropyl)amine.

7. The composition of claim 1 wherein component (b) is a mixture of N,N-bis-(2-hydroxypropyl)amine and N,N,N-tris-(2-hydroxypropyl)amine, wherein N,N,N-tris-(2-hydroxypropyl)amine must be presented to produce a clear homogenous product at ambient temperature.

8. The composition of claim 1 wherein component (b) is N-(2-hydroxypropyl)-N-(butyl)amine.

9. The composition of claim 1 wherein component (b) is N-(2-hydroxypropyl)-N-(2-hydroxybutyl)amine.

10. The composition of claim 7 which additionally contains N-(2-hydroxypropyl)amine.

11. The composition of claim 1 wherein compound (b) is 2,2-bis(hydroxymethyl)-2,2',2"-nitrilotriethanol.

12. The composition of claim 1 which is substantially free of lower alcohols.

13. The composition of claim 1 which is substantially free of ethanol.

14. The composition of claim 1 which is substantially free of higher alcohols.

15. The composition of claim 1 wherein component (a) is selected from the group consisting of alkyl sulfates, alkyl ether sulfates, olefin sulfonates, and alkyl benzene sulfonates, and mixtures thereof.

16. The composition of claim 15 which is an olefin sulfonate.

17. The composition of claim 15 which is an alkyl sulfate.

18. The composition of claim 15 which is a mixture of an alkyl sulfate and alkyl ether sulfate.

19. The composition of claim 15 wherein component (a) is an alkyl benzene sulfonate.

20. The composition of claim 15 wherein component (a) is an alkyl ether sulfate.

* * * * *

UNITED STATES PATENT AND TRADEMARK OFFICE
CERTIFICATE OF CORRECTION

PATENT NO. : 4,476,045
DATED : Oct. 9, 1984
INVENTOR(S) : Anthony J. O'Lenick

It is certified that error appears in the above-identified patent and that said Letters Patent are hereby corrected as shown below:

In column 6, line 60, after "amounts in the formulation given above:", insert:

-- Cocoamide diethanolamine --.

Signed and Sealed this

Sixteenth Day of April 1985

[SEAL]

Attest:

DONALD J. QUIGG

Attesting Officer

Acting Commissioner of Patents and Trademarks